US007998070B2

(12) United States Patent
Gentempo, Jr. et al.

(10) Patent No.: US 7,998,070 B2
(45) Date of Patent: Aug. 16, 2011

(54) QUANTIFYING NEUROSPINAL FUNCTION

(76) Inventors: Patrick Gentempo, Jr., Oakland, NJ (US); Lee Brody, Somerville, MA (US)

( * ) Notice: Subject to any disclaimer, the term of this patent is extended or adjusted under 35 U.S.C. 154(b) by 513 days.

(21) Appl. No.: 11/862,088

(22) Filed: Sep. 26, 2007

(65) Prior Publication Data

US 2008/0076979 A1 Mar. 27, 2008

Related U.S. Application Data

(60) Provisional application No. 60/847,164, filed on Sep. 26, 2006.

(51) Int. Cl.
*A61B 5/00* (2006.01)

(52) U.S. Cl. ........................................ 600/301

(58) Field of Classification Search .................. 600/300, 600/301, 587, 594, 595, 546, 549
See application file for complete search history.

(56) References Cited

U.S. PATENT DOCUMENTS

| | | | |
|---|---|---|---|
| 1,552,284 A | 1/1924 | Evins | |
| 1,610,271 A | 12/1926 | Evins | |
| 2,297,868 A | 10/1942 | Bergeron | |
| 2,546,276 A | 3/1951 | Redding | |
| 3,830,224 A | 8/1974 | Vanzetti et al. | |
| 3,830,970 A | 8/1974 | Hurley et al. | |
| 3,855,714 A | 12/1974 | Block | |
| 3,868,508 A | 2/1975 | Lloyd | |
| 3,970,074 A | 7/1976 | Mogos et al. | |
| 3,980,073 A | 9/1976 | Shaw, IV | |
| 4,010,367 A | 3/1977 | Suzuki | |
| 4,043,324 A | 8/1977 | Shaw, IV | |
| 4,055,166 A | 10/1977 | Simpson et al. | |
| 4,170,225 A | 10/1979 | Criglar et al. | |
| 4,186,748 A | 2/1980 | Schlager | |
| 4,218,707 A | 8/1980 | Reed et al. | |
| 4,323,351 A | 4/1982 | Goldsmith | |
| 4,347,854 A | 9/1982 | Gosline et al. | |
| 4,366,381 A | 12/1982 | Fischer et al. | |
| 4,379,461 A | 4/1983 | Nilsson et al. | |
| 4,428,382 A | 1/1984 | Walsall et al. | |
| 4,445,516 A | 5/1984 | Wollnik et al. | |
| 4,461,301 A | 7/1984 | Ochs | |
| 4,479,498 A | 10/1984 | Toftness | |
| 4,624,642 A | 11/1986 | Ferrera | |
| 4,664,130 A | 5/1987 | Gracovetsky | |

(Continued)

FOREIGN PATENT DOCUMENTS

SU   1066538   1/1984

OTHER PUBLICATIONS

Medical News Today, Biggest Breakthrough in Chiropractic Exam in Nearly Two Decades, Sep. 8, 2006.*

(Continued)

*Primary Examiner* — Max Hindenburg
*Assistant Examiner* — Brian Szmal
(74) *Attorney, Agent, or Firm* — Knobbe, Martens, Olson & Bear, LLP

(57) ABSTRACT

An aspect disclosed herein involves methods and systems for determining a neurospinal functional index (NSFI) provide a single index quantifying a plurality of neurospinal functions, for example, algometry, range of motion, electromyography, thermography, and heart rate variability. Embodiments of the NSFI are useful in providing an objective index of a patient's neurospinal function, for example, in chiropractic assessments.

16 Claims, 7 Drawing Sheets

U.S. PATENT DOCUMENTS

| | | | |
|---|---|---|---|
| 4,711,248 A | 12/1987 | Steuer et al. |
| 4,807,642 A | 2/1989 | Brown |
| 4,849,885 A | 7/1989 | Stillwagon et al. |
| 4,971,069 A | 11/1990 | Gracovetsky |
| 5,050,612 A | 9/1991 | Matsumura |
| 5,058,602 A | 10/1991 | Brody |
| 5,060,657 A | 10/1991 | Teague |
| 5,353,793 A | 10/1994 | Bornn |
| 6,398,740 B1 | 6/2002 | Lavery et al. |
| 6,440,084 B1 | 8/2002 | Gentempo et al. |
| 6,539,328 B1 | 3/2003 | Cremonese et al. |
| 6,595,934 B1 | 7/2003 | Hissong et al. |
| 6,785,574 B2 | 8/2004 | Kajitani et al. |
| 7,115,098 B2 | 10/2006 | Gentempo et al. |
| 7,438,466 B2 | 10/2008 | Gentempo et al. |
| 2002/0151817 A1 | 10/2002 | Gentempo et al. |
| 2006/0178588 A1 | 8/2006 | Brody |
| 2007/0147464 A1 | 6/2007 | Gentempo et al. |
| 2007/0249957 A1 | 10/2007 | Gentempo et al. |

OTHER PUBLICATIONS

Brochure for "Subluxation™ Station", Chiropractic Leadership Alliance, 2000.

U.S. Appl. No. 09/661,712, filed Sep. 14, 2000 (Patent No. 6,440,084, issued on Aug. 27, 2002), including its file history.

U.S. Appl. No. 10/173,336, filed Jun. 14, 2002 (Patent No. 7,115,098, issued on Oct. 3, 2006), including its file history.

U.S. Appl. No. 11/315,080, filed Dec. 22, 2005 (Pub. No. 2007/0178588 A1, published on Aug. 10, 2006), including its file history.

U.S. Appl. No. 11/615,875, filed Dec. 22, 2006 (Patent No. 7,438,466, issued on Oct. 21, 2008), including its file history.

U.S. Appl. No. 11/736,742, filed Apr. 18, 2007 (Pub. No. 2007/0249957 A1, published on Oct. 25, 2007), including its file history.

* cited by examiner

 NeuroSpinal Functional Index Report  Friday, June 09, 2006

Patient Information
First Name : Mike                    Last Name : Doe
Patient ID : 50                      Gender    : MALE
Height     : 67                      Birth Date : 01/14/1970

Office Information
Doctor  : Dr. John Doe
Address : 1234 Main Street Suite F Your City AA 01234
Phone   : 201-684-6789               Email  : info@subluxation.com On 03/01/2006, Mike Doe underwent a series of physical assessments to determine the state of health of core neurological and spinal functions.

The overall results of these tests are summarized in a single index which quantifies Neurospinal functions.

NeuroSpinal Functional Index: 81.48

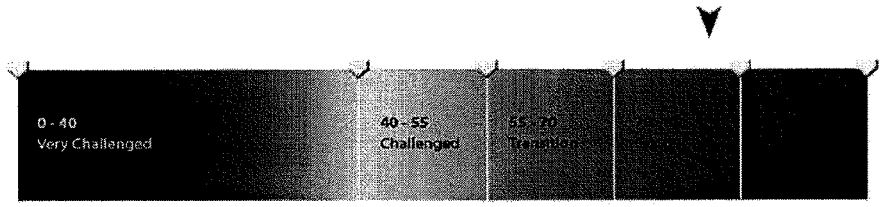

The graph below describes the results from each of the exams performed, and the following page details the exam protocols and results.

Exam Score Summary

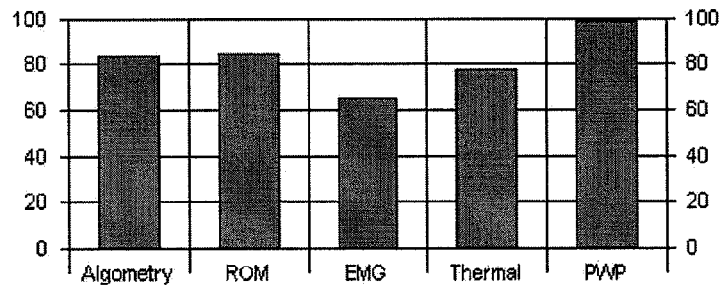

*FIG. 7*

QUANTIFYING NEUROSPINAL FUNCTION

CROSS REFERENCE TO RELATED APPLICATION

This application claims the benefit of U.S. Application No. 60/847,164 filed Sep. 26, 2006, the disclosure of which is incorporated by reference in its entirety.

BACKGROUND

1. Technical Field

This disclosure relates to a method of diagnosing and quantifying neurospinal function in humans.

2. Description of the Related Art

Chiropractors and other health care professionals currently utilize a multitude of tests in attempt to diagnose the function of the spine and nervous system. For instance, to evaluate the muscles that support the spine, many chiropractors use surface EMG devices to measure the muscle tone in the paraspinal muscles at a variety of locations along a patient's spinal column. Other chiropractors use an inclinometer to measure end-point range of motion in order to quantify the amount of motion in each region of the spine. Still others utilize an algometer to quantify sensitivity to pressure along the spinal column in order to diagnose the sensory nervous system.

The challenge that the chiropractor currently faces is the inability to easily integrate the results from different diagnostic tests in order to build a complete picture of neurospinal function.

SUMMARY OF THE INVENTION

An aspect of this disclosure involves methods and systems for determining a neurospinal functional index (NSFI), which provide a single index quantifying a plurality of neurospinal functions, such as, for example, algometry, range of motion, electromyography, thermography, and heart rate variability. Embodiments of the NSFI are useful in providing an objective index of a patient's neurospinal function, for example, in chiropractic assessments.

Some embodiments provide a method for determining a neurospinal functional index comprising: performing a plurality of neurospinal examinations on a patient, thereby providing a plurality of results from the examinations; quantifying results from the examinations; scaling the quantified results; and integrating the scaled results into a neurospinal functional index.

Other embodiments provide a system for determining a neurospinal functional index comprising: a data processing unit; and data storage media comprising machine readable instructions that when executed by the data processing unit, perform a method for determining a neurospinal functional index. The method for determining a neurospinal functional index comprises: performing a plurality of neurospinal examinations on a patient, thereby providing a plurality of results from the examinations; quantifying results from the examinations; scaling the quantified results to reference data; and integrating the scaled results into a neurospinal functional index.

In some embodiments, the plurality of neurospinal examinations comprises combinations of surface electromyography; spinal thermography; and heart rate variability. In some embodiments, the plurality of neurospinal examinations further comprises spinal algometry. In some embodiments, the plurality of neurospinal examinations further comprises spinal range of motion.

In some embodiments, quantifying results comprises comparing at least one of the results from the examinations to reference data. In some embodiments, scaling the quantified results comprises placing the quantified results on a common scale. In some embodiments, scaled results have similar population statistics. In some embodiments, integrating the scaled results comprises weighting the scaled results.

BRIEF DESCRIPTION OF THE DRAWINGS

These and other features, aspects and advantages will be better understood with reference to preferred embodiments, which are illustrated in the accompanying drawings. The illustrated embodiments are merely exemplary and are not intended to limit the scope. The drawings comprise seven figures.

FIG. 7 illustrates an embodiment of a Neurospinal Function Index Report.

DETAILED DESCRIPTION OF THE PREFERRED EMBODIMENT

Embodiments of a method and system quantify and integrate results of a plurality of spinal, physiological, and/or anatomical examinations and/or measurements into a single neurospinal functional index (NSFI). Embodiments of the NSFI are useful in assessing the state of a patient's core neurological and/or spinal functions. In other embodiments, the NSFI is useful for diagnosing one or more deficiencies in a patient's neurological and/or spinal functions.

Figure 1:
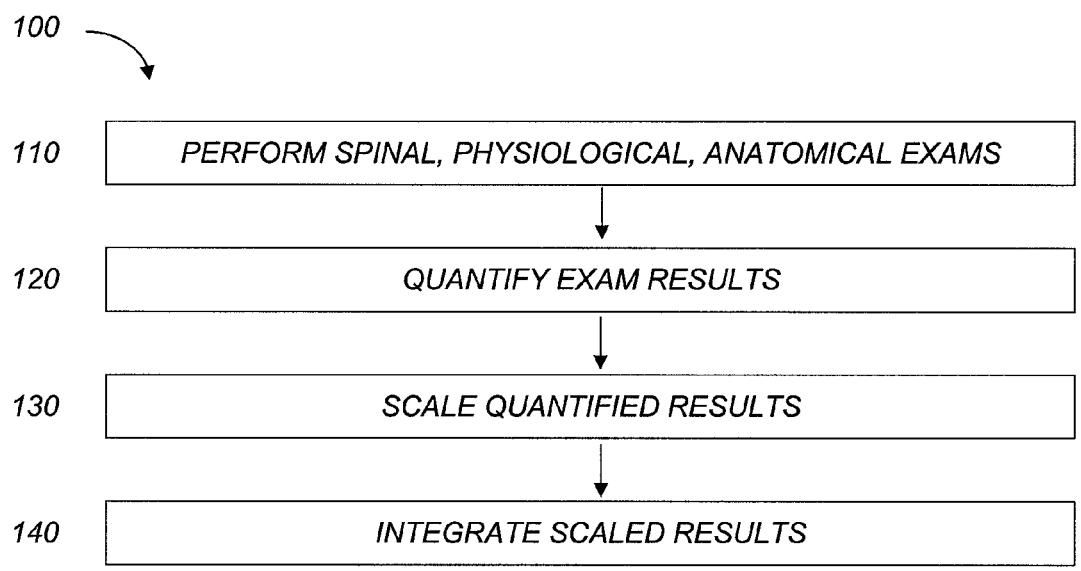
FIG. 1 illustrates an embodiment of a method for determining a neurospinal functional index.

An embodiment of a method for determining a neurospinal functional index is illustrated as a flowchart in FIG. 1. In step 110, a plurality of spinal, physiological, and/or anatomical examinations and/or measurements are performed. Some preferred embodiments include results from up to about five measurements, for example, (1) Spinal Algometry (Spinal Pain Mapping); (2) Spinal Range of Motion (Spinal Movement); (3) Surface EMG (Paraspinal muscle tension); (4) Spinal Thermography (Sympathetic Nervous System function); and (5) Heart Rate Variability (Autonomic Nervous System Activity and Balance).

In step 120, the results from each of the examinations are quantified by any suitable method known in the art. The particular method used to quantify the results of an examination will depend on factors known in the art, for example, the nature of the examination, the purpose of the examination, the method used in the examination, the nature of the results of the examination, and the like. In some embodiments, the quantified results are obtained through comparison of the examination results to reference data, discussed in greater detail below. For example, a range of motion examination of a patient's cervical extension may be 52°. The patient data is then compared with reference data, for example, for a particular age and gender, which in this example, is 87% of the reference value.

In step 130, the quantified results are put on a common scale. In some preferred embodiments, the scaling of the results comprises placing each of the scores for the examinations on the same scale, such that the scores for each of the examinations have similar population statistics, for example, using reference data obtained from a normative data collection study or from evaluating a large population of clinical data. For example, a reference data set was developed using the Insight Millennium from Chiropractic Leadership Alliance, Inc. (Mahwah, N.J.). Those skilled in the art will understand that other reference data sets are also useful in other embodiments. In some embodiments, these scaled results or subquotients are then compared for relative performance, thereby allowing a chiropractor to rank the results, for example, to identify facets of neurospinal function needing improvement. In some embodiments, the common scale is 0-100 or 0-1. Those skilled in the art will understand that other scales are used in other embodiments. In some embodiments, the scaling is incorporated into the next step, for example, by weighting or scaling functions and/or coefficients. Returning to the range of motion example, the patient's score is compared to the relevant population statistics. For example, if an 87% range of motion were within nearly every patient in the relevant population or subpopulation, for example, age and gender, then the particular patient would receive a low score in this step. On the other hand, if many patients' ranges of motion were below 87%, then 87% corresponds to a good score. In either case, the particular score will depend on the population statistics for the examination.

In step 140, the scaled results or subquotients are integrated to provide a neurospinal functional index. In some embodiments, the subquotients are integrated by taking an average, for example, a weighted average. Other embodiments use another method. The particular method will depend on factors including the particular examinations performed, distributions of the patient's scores, and the like.

Some embodiments provide a system for determining a Neurospinal Functional Index. In some embodiments, data from one or more of the examination procedures is automatically collected, for example, using an apparatus comprising a data collection and/or processing unit known in the art, for example, a computer, microcomputer, personal computer, workstation, microprocessor, embedded processor, combinations, and the like. In some preferred embodiments, the data processing unit also determines a Neurospinal Functional Index by implementing in software, hardware, and/or firmware one or more of the methods described herein. Some embodiments further comprise an output device known in the art, for example, a video display and/or a printer.

Described below are examples of preferred embodiments of spinal, physiological, and/or anatomical examinations and/or measurements useful in determining an embodiment of a neurospinal functional index, as well as particular embodiments for quantifying, scaling, and integrating these measurements.

The following Examples 1-5 describe embodiments of methods for determining the values of some preferred subquotients. Each of these Examples describes embodiments of steps 110, 120, and 130. Example 6 provides an embodiment of step 140 for determining an NSFI using the subquotients of Examples 1-5.

Example 1

Spinal Algometry

Spinal Pain Mapping

Figure 2:
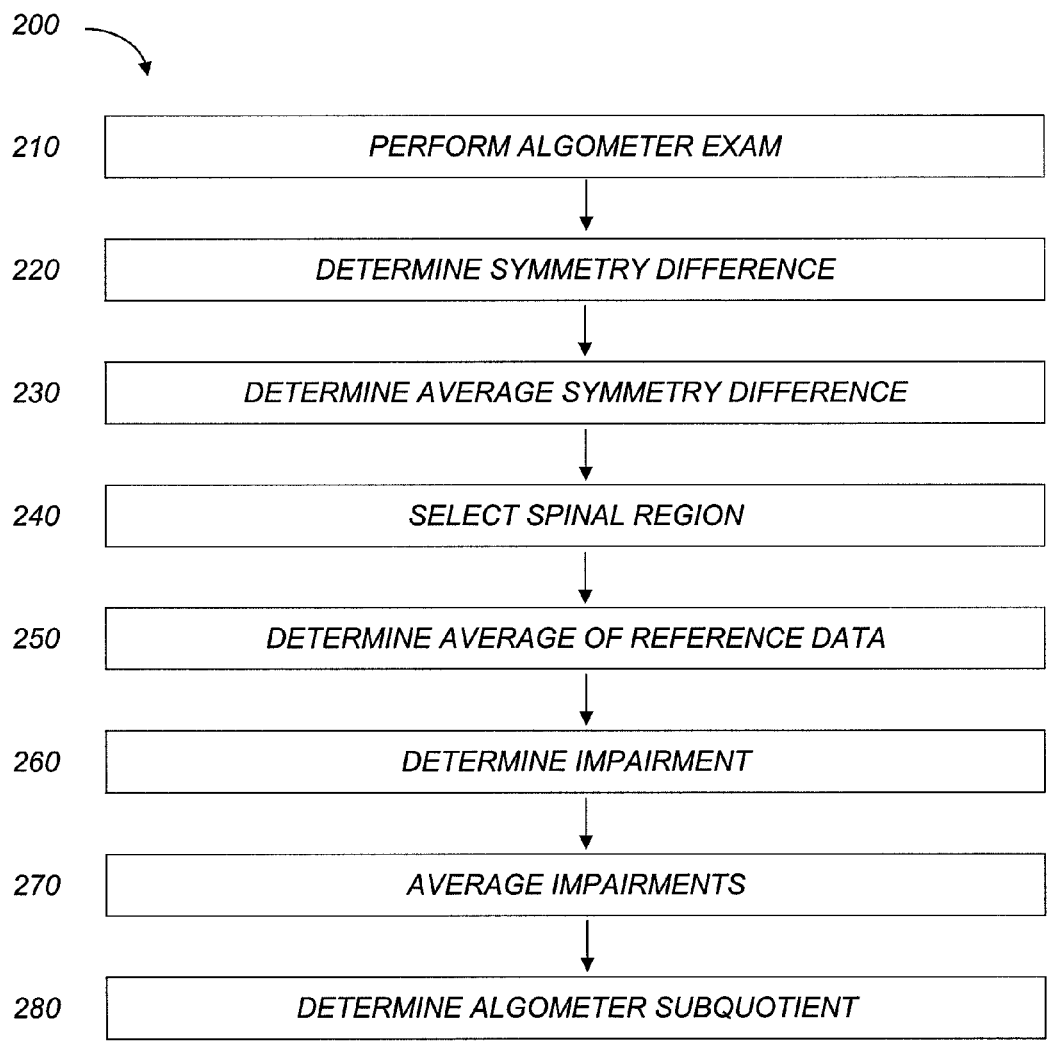
FIG. 2 illustrates an embodiment of a method for determining an Algometer Subquotient.

An embodiment of a method 200 for determining an Algometer Subquotient is illustrated in a flowchart in FIG. 2. In this example, the Algometer Subquotient includes data on two aspects of the algometer examination: (1) the left/right symmetry of the examination, and (2) a comparison of the data to the reference data of the examination. Note that some embodiments of the Algometer Subquotient do not include reference data or symmetry values. The inclusion or exclusion of one of these types of data depend on factors known in the art, for example, the presenting symptoms of the patient, the clinical focus of the chiropractor, and the like. In such cases, the Algometer Subquotient reflects only the data used in its calculation. An Algometer Subquotient that does not include either left/right symmetry data or reference data is typically not used in determining an NSFI.

In step 210, an algometer examination is performed. In one type of algometer examination, an examiner first palpates the patient's entire spine, identifying areas with heightened pressure sensitivity. After these areas are identified, non-symptomatic areas are identified as reference values. The examiner then places the tip of an algometer on one of the identified areas and slowly increases the pressure until the patient indicates that a pressure threshold is met. The analysis of these data can provide at least two-types of results: (1) asymmetry in the left/right symmetry of the pressure thresholds, and (2) impairment relative to the patient's own pressure sensitivity scale through comparison of the reference and sensitive areas. Other types of algometer examinations are also suitable, as would be appreciated by one skilled in the art.

In this example, the symmetry of the algometer examination data is calculated. In step 220, a "Symmetry Difference" is determine for each segment for which left and right data is available. An embodiment of a "Symmetry Difference" calculation for the left and right side data is provided in Eq. 1.

$$\text{Symmetry Difference} = \frac{|\text{Left} - \text{Right}|}{\left(\frac{\text{Left} + \text{Right}}{2}\right)} \qquad \text{Eq. 1}$$

In step 230, an "Average Symmetry Difference" for the patient can be calculated from all of the "Symmetry Differences" of the segments.

Algometer examination data is compared with reference data for each spinal region. In step 240, a region of the spine is selected, for example, the cervical, thoracic, and/or lumbar regions. In other embodiments, another region of the spine is selected, for example, one or more segments. In step 250, an arithmetic average of the reference data in the selected region is determined, providing an "average reference value." An impairment is determined in step 260, for example, as shown in Eq. 2. The "Data Value" and "Average Reference Value" are acquired as described above.

$$\text{Impairment} = \frac{\text{Data Value}}{\text{Average Reference Value}} \qquad \text{Eq. 2}$$

In the illustrated embodiment, if impairment>1, then the value is set to 1.

In step 270, an arithmetic average of the Impairments for all of the regions is determined, which is referred to as an "Average Impairment Value." In step 280, an "Algometer Subquotient" is determined, for example, according to Eq. 3.

Algometer Subquotient=100(½(Average Impairment Value)+½[1−(Average Symmetry Difference)]   Eq. 3

Example 2

Spinal Range of Motion

Spinal Movement

In an embodiment of a Spinal Range of Motion (ROM) Subquotient described in this Example, a patient's observed range of motion is compared with reference data, for example, as provided in *AMA Guides to the Evaluation of Permanent Disability, 5th Ed.*, the disclosure of which is incorporated by reference. Those skilled in the art will understand that other reference data is also useful in other embodiments.

Figure 3:
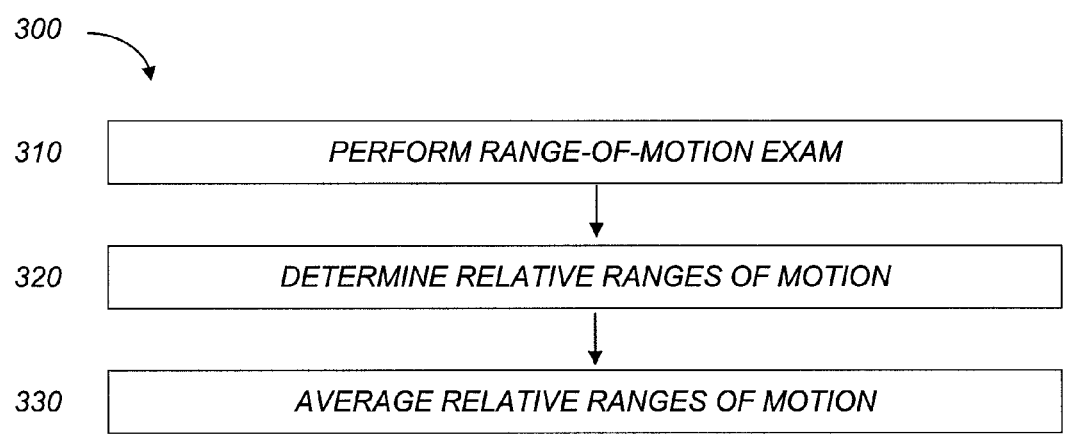
FIG. 3 illustrates an embodiment of a method for determining a Range of Motion Subquotient.

FIG. 3 is a flowchart illustrating an embodiment of a method 300 for determining a Spinal Range of Motion Subquotient. In step 310, an examiner performs one or more range of motion examinations on a patient, for example, selected from standard range-of-motion examinations of the spine known in the art, for example, as described in the American Medical Association's Guidelines to the Evaluation of Permanent Impairment, 5th Ed., the disclosure of which is incorporated by reference. In step 320, relative range-of-motion values are determined by comparing the results from each range-of-motion examination with the corresponding reference value, for example, as a percentage of the reference value. In the illustrated embodiment, where a patient's observed range of motion in an examination exceeds the reference value, that is, is greater than 100% of the reference value, the relative range-of-motion value is set to 100%. In step 330, the relative range-of-motion values are averaged to provide a Spinal Range of Motion Subquotient.

Example 3

Surface EMG

Paraspinal Muscle Tension

An embodiment of an electromyography (EMG) Subquotient described in this Example comprises the three scores from a Pattern Analysis of a patient: (1) Pattern Score, (2) Symmetry Score, and (3) Total Energy, which are described in U.S. Patent Application No. 60/793,208, filed Apr. 19, 2006, the disclosure of which is incorporated by reference, and a copy of which is filed herewith as EXHIBIT A. In the illustrated embodiment, the Pattern Score and Symmetry Score are already on a 0-100 scale, while Total Energy is on a different scale.

Figure 4:
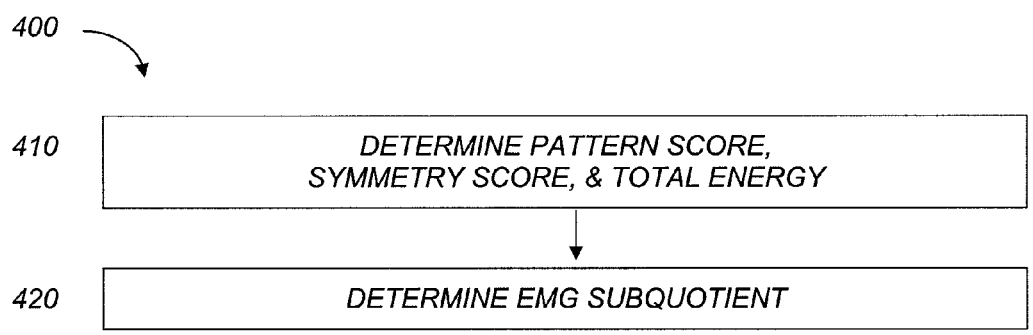
FIG. 4 illustrates an embodiment of a method for determining an EMG Subquotient.

An embodiment of a method 400 for determining an EMG Subquotient for a patient is illustrated in FIG. 4. In step 410, a Pattern Score, a Symmetry Score, and a Total Energy are determined for a patient. In step 420, an EMG Subquotient is determined as provided in TABLE 1.

TABLE 1

| Total Energy | EMG Subquotient |
|---|---|
| Total Energy < 50 | ³⁄₄[0.6(Pattern Score) + 0.4(Symmetry Score)] |
| 50 ≦ Total Energy < 75 | [¼ + 0.01(Total Energy)][0.6(Pattern Score) + 0.4(Symmetry Score)] |
| 75 ≦ Total Energy < 125 | (0.6(Pattern Score) + 0.4(Symmetry Score)) |
| 125 ≦ Total Energy < 150 | [2¼ − 0.01(Total Energy)][0.6(Pattern Score) + 0.4(Symmetry Score)] |
| Total Energy > 150 | ³⁄₄[0.6(Pattern Score) + 0.4(Symmetry Score)] |

Example 4

Spinal Thermography

Sympathetic Nervous System Function

An embodiment of a Thermal Subquotient is determined from spinal thermography data, for example, acquired using a thermal scanning device. Examples of suitable thermal scanners include the Insight Millennium Rolling Thermal Scanner (Chiropractic Leadership Alliance, Mahwah, N.J.) and TyTron C-3000 (Titronics Res. & Dev., Oxford, Iowa). The thermal scanner comprises a pair of thermal detectors, which are positioned on each side of a patient's spine, for example, at the base of the skull. The scanner is then moved along the patient's spine, collecting thermal data during the scanning. Generally, the scanning is terminated at the base of the spine. The thermal scan generates a set of pairwise thermal data corresponding to the temperature on the left and right sides of the spine over the scanned region of the spine. In some preferred embodiments, the temperature data correspond to spinal levels, segments, or vertebra. In this example, temperatures are given in °F., although those skilled in the art will understand that other temperature scales and/or values are also useful, for example, the electrical output of a thermal scanner.

Figure 5:
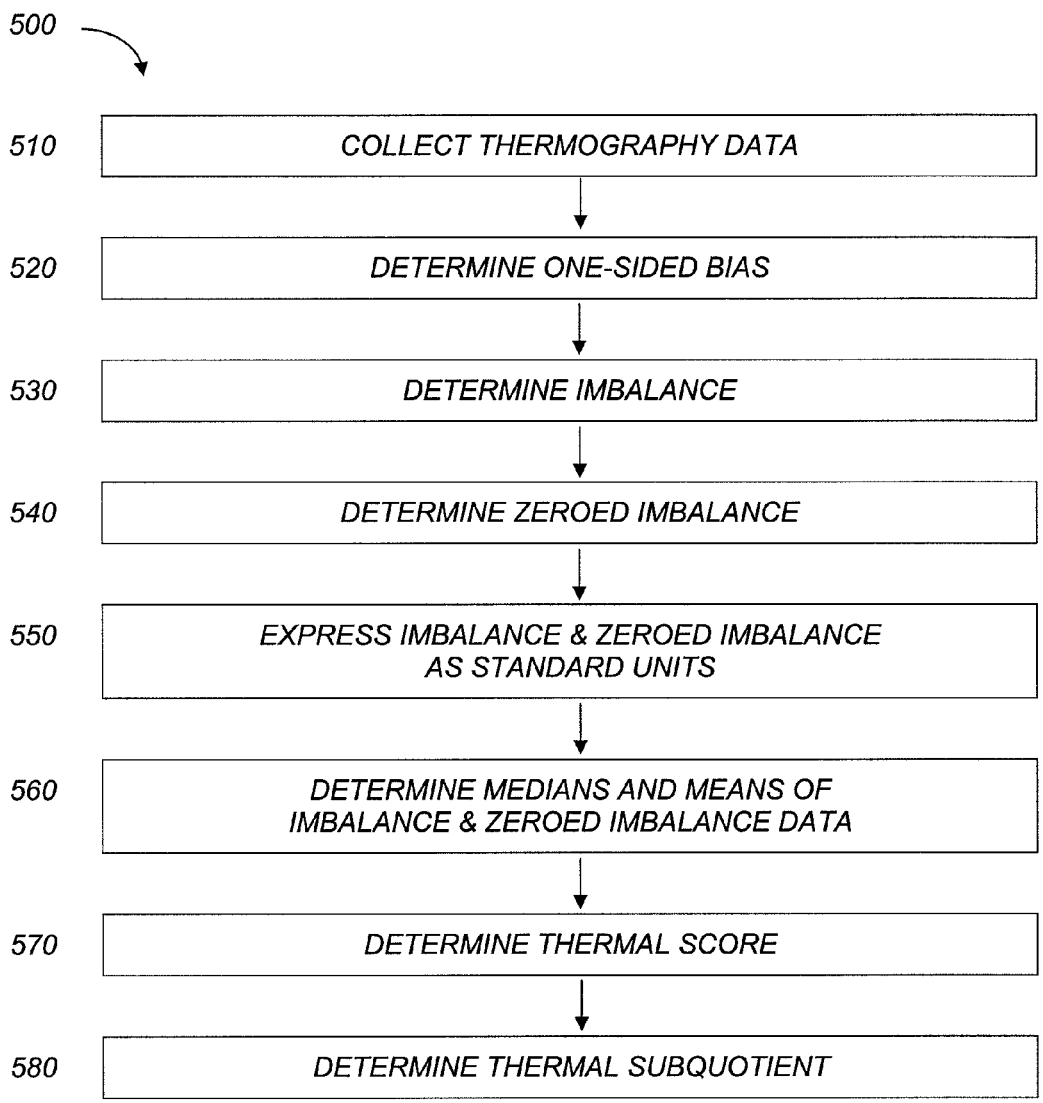
FIG. 5 illustrates an embodiment of a method for determining a Thermal Subquotient.
Figure 6:
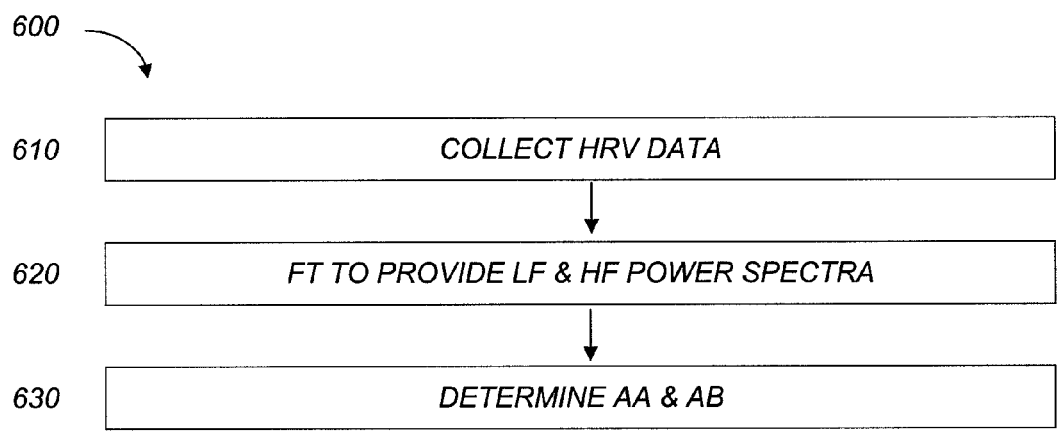
FIG. 6 illustrates an embodiment of a method for determining a PWP Subquotient.

In this Example, the Thermal Subquotient includes two components: (1) the total amount of imbalance in the scan; (2) the total amount of imbalance after the spinal thermography data is corrected to eliminate a one-sided bias ("zeroed"). FIG. 5 illustrates an embodiment of a method 500 for determining a Thermal Subquotient. In step 510, thermography data is collected in a thermography examination. In step 520, a One-Sided Bias of the thermography data is determined, for example, by taking the differences between the corresponding Left Side and Right Side Temperatures for each spinal level, and averaging the differences over the length of the scan. In general, the One-Sided Bias is between −2° F. and +2° F.

In step 530, an Imbalance is determined for each spinal level. In this Example, Imbalance is determined according to Eq. 4.

$$\text{Imbalance} = |\text{Left Temperature} - \text{Right Temperature}| \quad \text{Eq. 4}$$

In step 540, a Zeroed Imbalance is determined for each spinal level, for example, according to Eq. 5.

$$\text{Imbalance} = |(\text{Left Temperature} - \text{Right Temperature}) - (\text{One-Sided Bias})| \quad \text{Eq. 5}$$

In step 550, the Imbalance and Zeroed Imbalance are expressed in standard units, based on reference data by methods known in the art. Means and standard deviations (SD) for an exemplary set of reference data are provided in TABLE 2. Those skilled in the art will understand that other reference data are also useful in other embodiments. The result are pairs of Imbalance and Zeroed Imbalance for each spinal level in standard units.

TABLE 2

| Spinal Region | Mean (°F.) | Standard Deviation (°F.) |
|---|---|---|
| Cervical | 0.41 | 0.29 |
| Thoracic | 0.36 | 0.31 |
| Lumbar | 0.40 | 0.34 |
| Sacrum | 0.50 | 0.34 |

In step 560, the median and mean values for each of the Imbalance and the Zeroed Imbalance data sets are determined. The median values are insensitive to outliers, for example, at S1 or C1. The mean values reflect outlier data and the overall magnitude of deviations throughout the scan.

In step 570, a Thermal score is determined from the median and mean Imbalance and the Zeroed Imbalance values according to Eq. 6.

$$\text{Thermal Score} = 0.35 \frac{\text{Mean Zeroed Imbalance} + \text{Median Zeroed Imbalance}}{2} + 0.65 \frac{\text{Mean Imbalance} + \text{Median Imbalance}}{2} \quad \text{Eq. 5}$$

In step 580 a Thermal subquotient is determined from the Thermal score by converting to a 0-100 value according to TABLE 3.

TABLE 3

| Thermal Score | Thermal Subquotient |
|---|---|
| $0 \leq$ Thermal Score $\leq 4$ | 100 − [25(Thermal score)] |
| Otherwise | 0 |

Example 5

Heart Rate Variability

Autonomic Nervous System Activity and Balance

An embodiment of a Heart Rate Variability (Pulmonary Wedge Pressure, PWP) Subquotient determined in this Example comprises an Autonomic Activity Level (AA) and an Autonomic Balance Level (AB). A method 600 for determining a Heart Rate Variability Subquotient is illustrated in FIG. 600.

In step 610, a heart rate variability (HRV) data is collected from a patient, for example, as a series of interbeat intervals (IBI) taken in a five minute period. In step 620, the IBI data is Fourier transformed to provide Low Frequency (LF) and a High Frequency (HF) power spectra, for example, according to TABLE 4.

TABLE 4

| Band | Frequency Range |
|---|---|
| Low Frequency (LF) | about 0.04-0.15 Hz |
| High Frequency (HF) | about 0.15-0.4 Hz |

In step 630, AA and AB are calculated according to Eq. 6 and Eq. 7.

$$AA = 100 \frac{\ln(LF) + \ln(HF)}{19} \quad \text{Eq. 6}$$

$$AB = 100 \frac{1 - |LF - HF|}{\frac{LF + HF}{2}} \quad \text{Eq. 7}$$

In step 640, a Heart Rate Variability Subquotient is determine according to TABLE 5.

TABLE 5

| AA | Heart Rate Variability Subquotient |
|---|---|
| AA < 100 | 0.65(AA) + 0.35(AB) |
| AA $\geq$ 100 | 0.65 + 0.35(AB) |

Example 6

Neurospinal Functional Index

NSFI

In this Example, a Neurospinal Functional Index (NSFI) is determined from the subquotients of Examples 1-5 according to Eq. 8. This formula assigns weights to each of the subquotients based on the experiences of clinicians. Those skilled in the art will understand that other weightings are also possible.

$$NSFI = \tfrac{1}{4}\text{Thermal} + \tfrac{1}{4}\text{EMG} + \tfrac{1}{4}\text{PWP} + \tfrac{1}{8}\text{ROM} + \tfrac{1}{8}\text{Algometer} \quad \text{Eq. 8}$$

An embodiment of a Neurospinal Functional Index Report is illustrated in FIG. 7. In some embodiments, ranges of NSFI scores are assigned labels, for example, to provide a more descriptive result to a patient. For example, in the illustrated embodiment, ranges of scores were assigned the labels "Very Challenged," "Challenged," "Transition," "Good," and "Excellent" based on the population distribution of NSFI scores. Those skilled in the art will understand that different labels and/or different ranges are also useful in some embodiments. In addition to reporting a patient's Neurospinal Functional Index, the illustrated embodiment also provides summaries of the individual subquotients used in determining the Neurospinal Functional Index: algometry, range of motion (ROM), electromyography (EMG), thermography, and heart rate variability (PWP).

In some embodiments in which a patient does not exhibit any pressure sensitivity along the spinal column, the algometer examination is omitted and the Algometer Subquotient is set to 100.

In some embodiments in which a patient in pain is unable to complete a range-of-motion examination, the Range-of-Motion Subquotient is set to 50.

Examples of certain of the methods described herein use particular formulae and/or algorithms. Those skilled in the art will understand that the methods are not restricted to these formulae and/or algorithms. Those skilled in the art will also understand that examination results are quantifiable and/or scalable using other methods. Furthermore, other embodiments include at least one examination providing the same or similar patient information as at least one of the examinations discussed above.

Those skilled in the art will also understand that changes in the systems, devices, and processes described above are possible, for example, adding and/or removing components and/or steps, and/or changing their orders. Moreover, while the above detailed description has shown, described, and pointed out novel features as exemplified in various embodiments, it will be understood that various omissions, substitutions, and changes in the form and details of the systems, devices, and/or processes illustrated may be made by those skilled in the art without departing from the spirit of the disclosure. As will be recognized, some embodiments do not provide all of the features and benefits set forth herein, as some features may be used or practiced separately from others.

What is claimed is:

1. A method for determining a neurospinal functional index comprising:

using two or more devices to perform a plurality of neurospinal examinations on a patient, thereby providing a plurality of results from the examinations to a computer;

quantifying, by the computer, results from the examinations;

scaling, by the computer, the quantified results; and integrating, by the computer, the scaled results into a neurospinal functional index.

2. The method of claim 1, wherein the plurality of neurospinal examinations comprises combinations of surface electromyography; spinal thermography; and heart rate variability.

3. The method of claim 2, wherein the plurality of neurospinal examinations further comprises spinal algometry.

4. The method of claim 2, wherein the plurality of neurospinal examinations further comprises spinal range of motion.

5. The method of claim 1, wherein quantifying results comprises comparing at least one of the results from the examinations to reference data.

6. The method of claim 1, wherein scaling the quantified results comprises placing the quantified results on a common scale.

7. The method of claim 6, wherein scaled results have similar population statistics.

8. The method of claim 1, wherein integrating the scaled results comprises weighting the scaled results.

9. An apparatus for determining a neurospinal functional index comprising:

a data processing unit; and a non-transitory data storage media storing machine readable instructions that, when executed by the data processing unit, perform a computerized method for determining a neurospinal functional index comprising:

receiving results from a plurality of neurospinal examinations;

quantifying results from the examinations;

scaling the quantified results to reference data; and integrating the scaled results into a neurospinal functional index.

10. The apparatus of claim 9, wherein the plurality of neurospinal examinations comprises combinations of surface electromyography, spinal thermography; and heart rate variability.

11. The apparatus of claim 10, wherein the plurality of neurospinal examinations further comprises spinal algometry.

12. The apparatus of claim 10, wherein the plurality of neurospinal examinations further comprises spinal range of motion.

13. The apparatus of claim 9, wherein quantifying results comprises comparing at least one of the results from the examinations to reference data.

14. The apparatus of claim 9, wherein scaling the quantified results comprises placing the quantified results on a common scale.

15. The apparatus of claim 14, wherein the scaled results have similar population statistics.

16. The apparatus of claim 9, wherein integrating the scaled results comprises weighting the scaled results.

\* \* \* \* \*